US012484915B2

(12) United States Patent
Aneja et al.

(10) Patent No.: US 12,484,915 B2
(45) Date of Patent: Dec. 2, 2025

(54) ANTEGRADE RETROGRADE RECON FEMORAL INTRAMEDULLARY NAIL SYSTEM

(71) Applicant: University of Kentucky Research Foundation, Lexington, KY (US)

(72) Inventors: Arun Aneja, Lexington, KY (US); Lorenzo Deveza, Houston, TX (US); Shea Comadoll, Lexington, KY (US); Boshen Liu, Lexington, KY (US)

(73) Assignee: University of Kentucky Research Foundation, Nashville, TN (US)

( * ) Notice: Subject to any disclaimer, the term of this patent is extended or adjusted under 35 U.S.C. 154(b) by 142 days.

(21) Appl. No.: 18/370,760

(22) Filed: Sep. 20, 2023

(65) Prior Publication Data

US 2024/0008881 A1 Jan. 11, 2024

Related U.S. Application Data

(63) Continuation-in-part of application No. 16/601,678, filed on Oct. 15, 2019, now abandoned.

(Continued)

(51) Int. Cl.

| | |
|---|---|
| ***A61B 17/72*** | (2006.01) |
| ***A61B 17/17*** | (2006.01) |
| *A61B 17/56* | (2006.01) |

(52) U.S. Cl.

CPC ...... *A61B 17/1721* (2013.01); *A61B 17/1717* (2013.01); *A61B 17/1725* (2013.01); *A61B 2017/564* (2013.01)

(58) Field of Classification Search

CPC ........ A61B 17/1717–1725; A61B 17/72–7291

See application file for complete search history.

(56) References Cited

U.S. PATENT DOCUMENTS

| | | | |
|---|---|---|---|
| 3,709,218 A | 1/1973 | Halloran et al. | |
| 5,176,681 A * | 1/1993 | Lawes | A61B 17/744 606/65 |

(Continued)

FOREIGN PATENT DOCUMENTS

| | | |
|---|---|---|
| EP | 496950 A1 | 8/1992 |
| EP | 1344494 A2 | 9/2003 |
| WO | WO2010140991 A2 | 12/2010 |

OTHER PUBLICATIONS

Expert Retrograde/Antegrade Femoral Nail Surgical Technique article; DePuy Synthes (2016).

(Continued)

*Primary Examiner* — Eduardo C Robert

*Assistant Examiner* — Steven J Cotroneo

(74) *Attorney, Agent, or Firm* — Stites & Harbison PLLC; Warren D. Schickli

(57) ABSTRACT

A femoral intramedullary device is capable of treating a variety of femoral bone fractures. The device includes an intramedullary nail capable of antegrade or retrograde insertion into the femur and having a shank long enough to extend into the shaft of the long bone and reach the corresponding distal area or proximal area and sockets located intermediate the ends of the shank for receiving anchoring pins or screws extended transversely or radially from the shaft of the long bone. The intramedullary nail is placed in the intramedullary canal of a portion of the bone and the screws are fixed in the radial sockets or receivers at the level of the femoral neck to provide mechanical support across the bone. Transverse screws are placed through the transverse sockets to provide additional support and secure the nail within the femur.

10 Claims, 10 Drawing Sheets

Related U.S. Application Data

(60) Provisional application No. 62/745,770, filed on Oct. 15, 2018.

(56) References Cited

U.S. PATENT DOCUMENTS

| | | | | |
|---|---|---|---|---|
| 5,480,402 | A | 1/1996 | Kim | |
| 5,779,705 | A | 7/1998 | Matthews | |
| 6,010,506 | A | 1/2000 | Gosney et al. | |
| 6,120,504 | A | 9/2000 | Brumback | |
| 6,443,954 | B1 | 9/2002 | Bramlet | |
| 6,869,434 | B2 * | 3/2005 | Choi | A61B 17/1721 606/97 |
| 6,932,818 | B2 | 8/2005 | Behrens | |
| 7,041,104 | B1 | 5/2006 | Cole et al. | |
| 8,114,079 | B2 | 2/2012 | Haidukewych et al. | |
| 8,202,276 | B2 | 6/2012 | Fernandez | |
| 8,241,286 | B2 * | 8/2012 | Metzinger | A61B 17/72 606/86 R |
| 8,394,103 | B2 * | 3/2013 | O'Reilly | A61B 17/1703 606/104 |
| 8,764,752 | B2 | 7/2014 | Buettler | |
| 8,864,771 | B2 | 10/2014 | Buscher | |
| 8,986,315 | B2 | 3/2015 | Durante | |
| 9,220,544 | B2 | 12/2015 | Matityahu | |
| 9,421,049 | B2 * | 8/2016 | Rogachefsky | A61B 17/7208 |
| 9,943,346 | B2 | 4/2018 | Elghazaly et al. | |
| 10,251,691 | B2 | 4/2019 | Hedgeland | |
| 10,492,803 | B2 * | 12/2019 | Machamer | A61B 17/72 |
| 2003/0069581 | A1 | 4/2003 | Stinson et al. | |
| 2003/0073999 | A1 * | 4/2003 | Putnam | A61B 17/7291 606/62 |
| 2005/0096656 | A1 * | 5/2005 | Behrens | A61B 17/1721 606/64 |
| 2007/0123875 | A1 * | 5/2007 | Czartoski | A61B 17/744 606/62 |
| 2007/0270846 | A1 | 11/2007 | Metzinger | |
| 2008/0281331 | A1 * | 11/2008 | Fritzinger | A61B 17/1725 606/62 |
| 2009/0326541 | A1 | 12/2009 | Metzinger | |
| 2010/0286692 | A1 | 11/2010 | Greenhalgh et al. | |
| 2011/0295255 | A1 | 12/2011 | Roberts et al. | |
| 2012/0022533 | A1 | 1/2012 | Beuttler | |
| 2012/0197255 | A1 * | 8/2012 | Elghazaly | A61B 17/725 606/64 |
| 2012/0209268 | A1 | 8/2012 | Overes | |
| 2012/0330313 | A1 | 12/2012 | Grady | |
| 2014/0249536 | A1 | 9/2014 | Jajeh | |
| 2018/0078292 | A1 * | 3/2018 | Hedgeland | A61B 17/725 |
| 2019/0038326 | A1 | 2/2019 | Hedgeland et al. | |
| 2021/0346075 | A1 * | 11/2021 | Daly | A61B 17/1725 |

OTHER PUBLICATIONS

T2 Femoral Nailing System Operative Technique; Stryker Trauma GmbH (2016).

* cited by examiner

ANTEGRADE RETROGRADE RECON FEMORAL INTRAMEDULLARY NAIL SYSTEM

RELATED APPLICATION

This application is a continuation-in-part (CIP) of U.S. patent application Ser. No. 16/601,678, filed on Oct. 15, 2019, which claims priority to U.S. Provisional Patent Application 62/745,770 filed on Oct. 15, 2018, the full disclosures of which are hereby incorporated by reference in their entirety.

TECHNICAL FIELD

This document relates to the field of bone fracture and impending fracture stabilization treatment. More particularly, this document pertains to the fixation of femoral fractures and/or impending fractures with involvement of femoral neck and/or intertrochanteric and/or subtrochanteric and/or diaphyseal and/or metaphyseal and/or condylar region using an intramedullary rod/nail system.

BACKGROUND

Intramedullary nails have been used in the treatment and stabilization of fractures of the long bones including the femur. In order to stabilize and/or treat a fracture of the femur an intramedullary nail may be inserted into the canal of the femur either in a retrograde or antegrade fashion and be positioned to extend across the fracture line. Following insertion, screws, bolts, blades and/or other devices may be inserted across the femur and nail through pre-made sockets in order to secure the nail within the femur and stabilize the two or multiple ends of fractures.

Although intramedullary nails have commonly been used to treat femoral shaft fractures, recent modifications to the intramedullary nail have allowed it to be used to treat other fractures and/or impending fractures of the femur including the femoral neck.

Another intramedullary system has a lag screw assembly that attaches to an intramedullary nail and allows for compression of femoral neck and intertrochanteric fractures.

Similar devices with antegrade insertion use parallel screws inserted proximally to provide stabilization in the case of femoral neck fracture.

A patient with fractures of the distal femur or with multiple injuries benefits from a nail inserted in a retrograde fashion through the distal end of the femur with proximal interlocking screws inserted in the diaphyseal region of the proximal femur.

Though the options currently available allow for nails to be inserted in a retrograde fashion, which allows for speed and ease of access, and an antegrade fashion, which allows for neck and trochanteric region stabilization, there is not a nail that allows for both retrograde and anterograde insertion with options for neck and trochanteric region stabilization.

The present femoral intramedullary device seeks to provide a solution to the problem(s) by providing the ability to insert an intramedullary nail in either a retrograde or antegrade fashion while having options for neck and/or trochanteric fixation and/or stabilization. The described intramedullary nail has an elongated body with multiple transverse and oblique receivers or sockets extending through the first and second ends of the nail. These receivers/sockets may be configured for receiving lag screws and/or helical blades and/or conventional interlocking screws and/or bolts and/or other locking screws and/or other devices with the capability to form a fixed or compressible angle device. The intramedullary nail may be inserted in either an antegrade or retrograde fashion and has receivers or sockets on bilateral ends that will allow for screws and/or other devices placed through the nail in a percutaneous fashion through a guide/outrigger that attaches to the nail. The placement of these interlocking screws or devices will assist with stabilization of the femoral neck and/or trochanteric and/or subtrochanteric and/or metaphyseal and/or diaphyseal and/or distal condylar regions of the femur.

By having multiple transverse and obliquely oriented receivers/sockets on each end of the nail with the capability of securing interlocking devices at various angles, the overall utility of the nail and spectrum of fractures for which it may be used in treatment is increased. This also allows for fixation of multiple or segmental femur fractures using a retrograde or antegrade approach with the benefit of stabilization of the femoral neck and trochanteric region.

In addition, this nail comes with a long guide/outrigger that can be screwed or secured by other means onto either end of the nail and allows targeted placement of the various interlocking screw at various angles or device options. The long guide/outrigger may be secured to the diaphyseal portion of the nail via wire or drill bits placed through the guide/outrigger and through the receivers of the nail allowing for further stabilization of the outrigger to allow for optimal screw/blade/bolt/device placement. This obviates the likelihood of the outrigger missing the proximal or distal end of the screws/blades/devices.

SUMMARY

In accordance with the purposes and benefits described herein, a new and improved femoral intramedullary device is provided. That device comprises: (a) an intramedullary nail configured for antegrade or retrograde insertion into the intramedullary canal of a femur and (b) a plurality of fasteners. The intramedullary nail has an elongated body including a first end, a second end and a plurality of oblique fastener receivers wherein at least one of the plurality of oblique fastener receivers is provided at the first end and at least one of the plurality of oblique fastener receivers is provided at the second end. At least one fastener of the plurality of fasteners is received in the oblique fastener receiver (a) in the first end to stabilize a neck of the femur when the intramedullary nail is retrograde inserted into the femur or (b) in the second end to stabilize the neck of the femur when the intramedullary nail is antegrade inserted into the femur.

The femoral intramedullary device may also include a guide adapted for placement of the plurality of fasteners with respect to the intramedullary nail. That guide may include at least one oblique fastener locator aligned with the oblique fastener receiver (a) in the first end when the intramedullary nail is retrograde inserted into the femur and (b) in the second end when the intramedullary nail is antegrade inserted into the femur.

One or more embodiments of the femoral intramedullary device may also include at least one stabilizer pin receiver in the guide aligned with at least one transverse stabilizer socket in the elongated body between the plurality of oblique fastener receivers in the first end and the second end.

The femoral intramedullary device may further include at least one stabilizer pin received in the at least one stabilizer pin receiver and the at least one transverse stabilizer socket. This structural arrangement functions to stabilize the intramedullary nail in position in the intramedullary canal of the femur. This structural arrangement also properly aligns the at least one oblique fastener locator with the oblique fastener receiver (a) in the first end when the intramedullary nail is retrograde inserted into the femur and (b) in the second end when the intramedullary nail is antegrade inserted into the femur.

In one or more of the many possible embodiments, the guide may be substantially J-shaped and include a lug at a terminal end thereof. That lug may be adapted to engage in a lug receiver in the second end of the intramedullary nail.

The plurality of fasteners used to secure the intramedullary nail in the femur and stabilize the femur may be of any type known in the art to be useful for such a purpose. Thus, for example, the plurality of fasteners may be selected from a group consisting of at least one screw, at least one helical blade, at least one bolt, at least one compression screw, at least one wire, at least one pin, at least one bone fixation device or combinations thereof.

The femoral intramedullary device may further include a transverse guide sleeve received in the at least one stabilizer pin receiver and extending at least partially between the at least one stabilizer pin receiver in the guide and the at least one transverse stabilizer socket in the intramedullary nail. The femoral intramedullary device may further include an oblique guide sleeve received in the at least one oblique fastener locator in the guide and extending at least partially between that at least one oblique fastener locator and the oblique fastener receiver in the intramedullary nail.

In accordance with yet another aspect, a new and improved method of fixing a fractured femur comprises: (a) orienting an intramedullary nail configured for antegrade or retrograde insertion into an intramedullary canal of the femur, (b) inserting the intramedullary nail into the intramedullary canal of the femur so as to extend across a fracture line of the femur and (c) engaging at least one fastener in an oblique fastener receiver in a first end of the intramedullary nail to stabilize the neck of the femur when the intramedullary nail is retrograde inserted into the femur or in a second end of the intramedullary nail to stabilize the neck of the femur when the intramedullary nail is antegrade inserted into the femur.

The method may further include the step of mounting the intramedullary nail onto a guide by engaging a lug on the guide with a lug receiver at the second end of the intramedullary nail.

The method may include the step of inserting a stabilizer pin into a stabilizer pin receiver in the guide and a transverse stabilizer socket of the intramedullary nail before engaging the at least one fastener in the oblique fastener receiver in order to stabilize the intramedullary nail in the intramedullary canal of the femur and to properly align the oblique fastener locator in the guide with the oblique fastener receiver (a) in the first end when the intramedullary nail is retrograde inserted into the femur and (b) in the second end when the intramedullary nail is antegrade inserted into the femur.

Still further, the method may include the step of positioning a transverse guide sleeve between the stabilizer pin receiver in the guide and the transverse stabilizer socket in the intramedullary nail prior to inserting the stabilizer pin.

The method may also include the step of positioning an oblique guide sleeve between the oblique fastener locator in the guide and the oblique fastener receiver in the intramedullary nail before engaging the at least one fastener in the oblique fastener receiver (a) in the first end of the intramedullary nail to stabilize the neck of the femur when the intramedullary nail is retrograde inserted into the femur and (b) in the second end when the intramedullary nail is antegrade inserted into the femur.

The method may also include the step of extending the at least one fastener into a neck of the femur to engage the neck and thereby stabilize the neck.

In accordance with yet another aspect, a new and improved method is provided for fixing a fractured femur. That method comprises, consists of or consists essentially of: (a) orienting an intramedullary nail for retrograde insertion into an intramedullary canal of the fractured femur, (b) using a center of a intercondylar notch in a coronal plane of the fractured femur as a starting point and inserting a first end of the intramedullary nail into the intramedullary canal so as to extend across a fracture line of the fractured femur, and (c) engaging at least one fastener at an oblique angle into a neck of the fractured femur.

In at least some embodiments, the method also includes mounting the intramedullary nail onto a guide by engaging a lug on the guide with a lug receiver at the second end of the intramedullary nail prior to the orienting of the intramedullary nail.

Various embodiments of the method include inserting a stabilizer pin into a stabilizer pin receiver in the guide and a transverse stabilizer socket of the intramedullary nail to stabilize the intramedullary nail in the intramedullary canal of the fractured femur and to properly align an oblique fastener locator in the guide with an oblique fastener receiver in the first end of the intramedullary nail prior to the engaging at least one fastener at an oblique angle into a neck of the fractured femur. Such embodiments may include positioning a transverse guide sleeve between the stabilizer pin receiver in the guide and the transverse stabilizer socket in the intramedullary nail prior to inserting the stabilizer pin.

In at least one of the many possible embodiments, the method includes positioning an oblique guide sleeve between the oblique fastener locator in the guide and the oblique fastener receiver in the intramedullary nail before engaging the at least one fastener in the oblique fastener receiver in the first end of the intramedullary nail to stabilize the neck of the fractured femur. In at least some embodiments, the method includes extending the at least one fastener into the neck of the fractured femur to thereby stabilize the neck.

In at least some embodiments, the method includes stabilizing an outrigger in position alongside the femur so that an oblique fastener locator in the outrigger and an oblique fastener receiver in the intramedullary nail are both aligned with and adapted to match a native angle of the femoral neck of the fractured femur when the fractured femur has been realigned for setting.

Such a method may further include locating and inserting at least one fastener into the femoral neck using the oblique fastener locator and the oblique fastener receiver to guide the fastener into position.

In accordance with yet another aspect, a new and improved femoral intramedullary system, comprises, consists of or consists essentially of: (a) an intramedullary nail having a first end configured for retrograde insertion into a fractured femur, the intramedullary nail having an elongated body including at least one oblique fastener receiver at the first end, wherein that at least one fastener receiver is adapted to match a native angle of a femoral neck of the fractured femur when the fractured femur has been realigned for setting and (b) at least one fastener received in the at least one oblique fastener receiver and the femoral neck of the fractured femur to stabilize a neck of the femur.

In at least some of the many possible embodiments, the femoral intramedullary system includes (a) a guide adapted for placement of the at least one fastener with respect to the intramedullary nail, (b) at least one stabilizer pin receiver in the guide aligned with at least one transverse stabilizer socket in the elongated body, and (c) at least one stabilizer pin received in the at least one stabilizer pin receiver and the at least one transverse stabilizer socket whereby the intramedullary nail is stabilized in an intramedullary canal of the femur and the at least one oblique fastener locator is properly aligned with the at least one oblique fastener receiver.

In at least one possible embodiment, the femoral intramedullary system, the guide is a J-shaped outrigger including a lug at a terminal end thereof adapted to engage in a lug receiver in a second end of the intramedullary nail. In at least one possible embodiment, the femoral intramedullary system further includes a transverse guide sleeve extending at least partially between the at least one stabilizer pin receiver in the guide and the at least one transverse stabilizer socket in the intramedullary nail. In some embodiments, the femoral intramedullary system further includes an oblique guide sleeve extending at least partially between the at least one oblique fastener locator in the guide and the at least one oblique fastener receiver in the intramedullary nail.

In at least one of the many possible embodiments, the oblique fastener locator and the oblique fastener receiver are aligned to match a native angle of a femoral neck of the fractured femur at an anteversion angle of between about 5 degrees and about 25 degrees. In some embodiments, the oblique fastener locator and the oblique fastener receiver are aligned to match a native angle of a femoral neck of the fractured femur at an anteversion angle of between about 10 degrees and about 20 degrees. In some embodiments, the oblique fastener locator and the oblique fastener receiver are aligned to substantially match a native angle of a femoral neck of the fractured femur at an anteversion angle of about 15 degrees. In some embodiments, the oblique fastener receiver is adapted to extend on a line forming an acute included angle of between about 5 degrees and about 25 degrees with a coronal plane the fractured femur.

In the following description, there are shown and described several preferred embodiments of the femoral intramedullary device and the related method of fixing a fractured femur. As it should be realized, the femoral intramedullary device and the related method are capable of other, different embodiments and their several details are capable of modification in various, obvious aspects all without departing from the device and method as set forth and described in the following claims. Accordingly, the drawings and descriptions should be regarded as illustrative in nature and not as restrictive.

BRIEF DESCRIPTION OF THE DRAWING FIGURES

Some embodiments of the present invention are illustrated as an example and are not limited by the figures of the accompanying drawings, in which like references may indicate similar elements and in which.

Figures 4A, 4B, 4C:
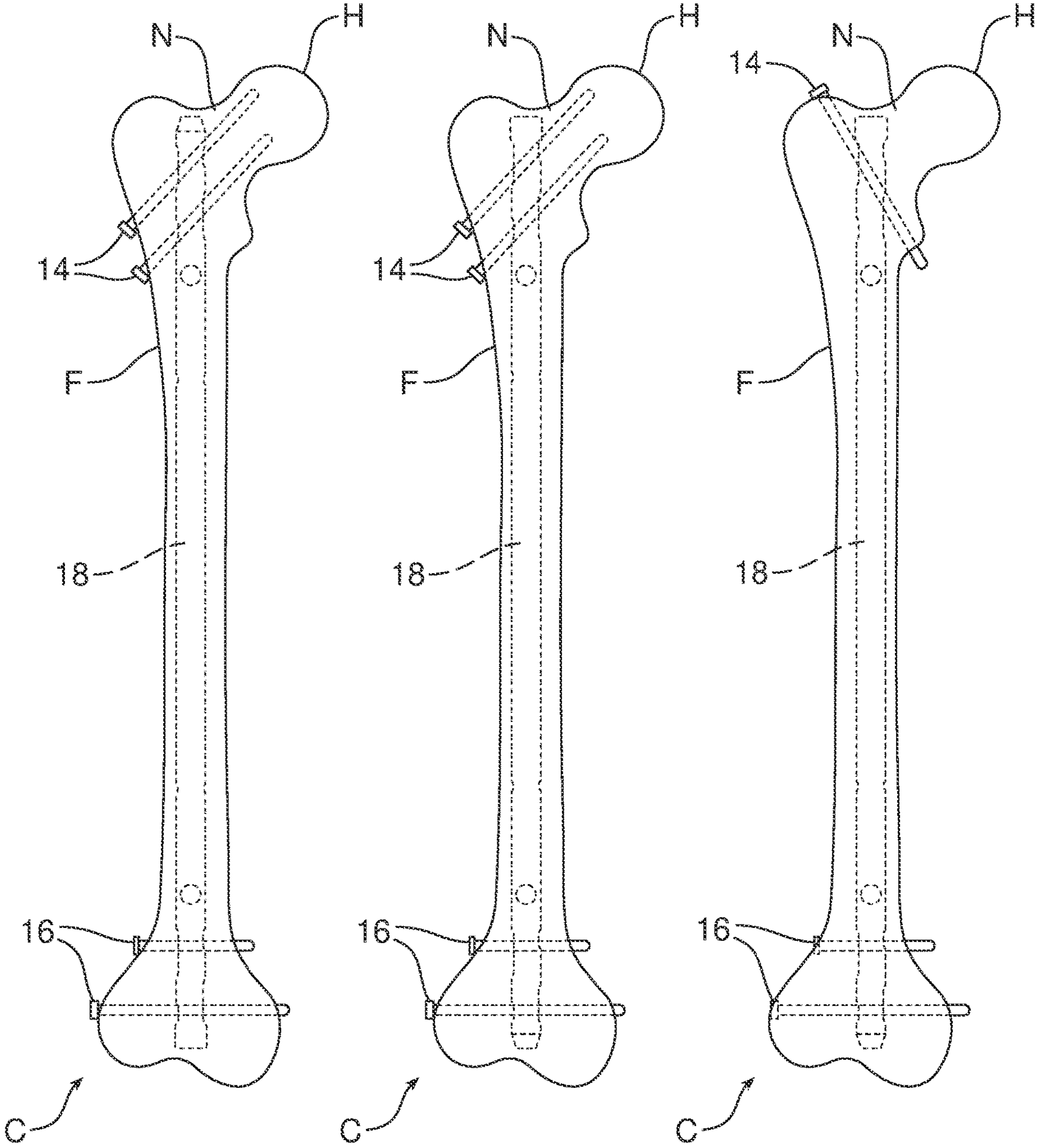
FIGS. 4A-4C depict views, in longitudinal cross section, of the intramedullary nail placed in the intramedullary canal of a femur using various intramedullary device options.

More particularly, FIG. 4A depicts a view, in longitudinal cross section, of the intramedullary nail placed in the intramedullary canal of a fractured femur using a retrograde method of insertion with cortical screws placed to stabilize the nail within the canal with stabilization of the femoral neck.

FIG. 4B depicts a view, in longitudinal cross section, of the intramedullary nail placed in the intramedullary canal of a fractured femur using an antegrade method of insertion with cortical screws placed to stabilize the nail within the canal with stabilization of the femoral neck.

FIG. 4C depicts a view, in longitudinal cross section, of the intramedullary nail placed in the intramedullary canal of a fractured femur using an antegrade method of insertion with cortical screws placed to stabilize the nail within the canal without stabilization of the femoral neck.

Figure 5:
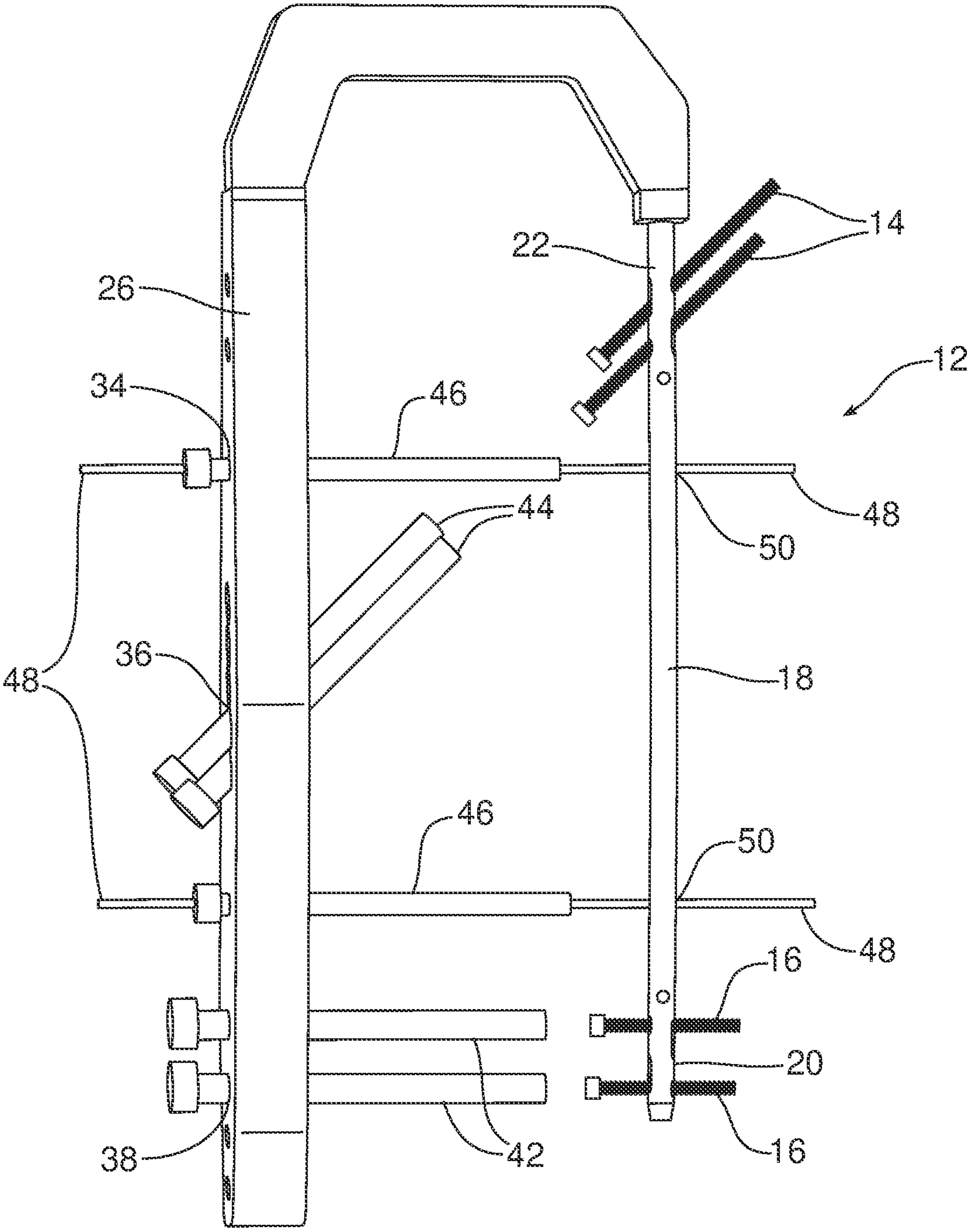

FIG. 5 depicts a longitudinal view of the femoral intramedullary device with attached guide configured for antegrade insertion.

Figure 6:
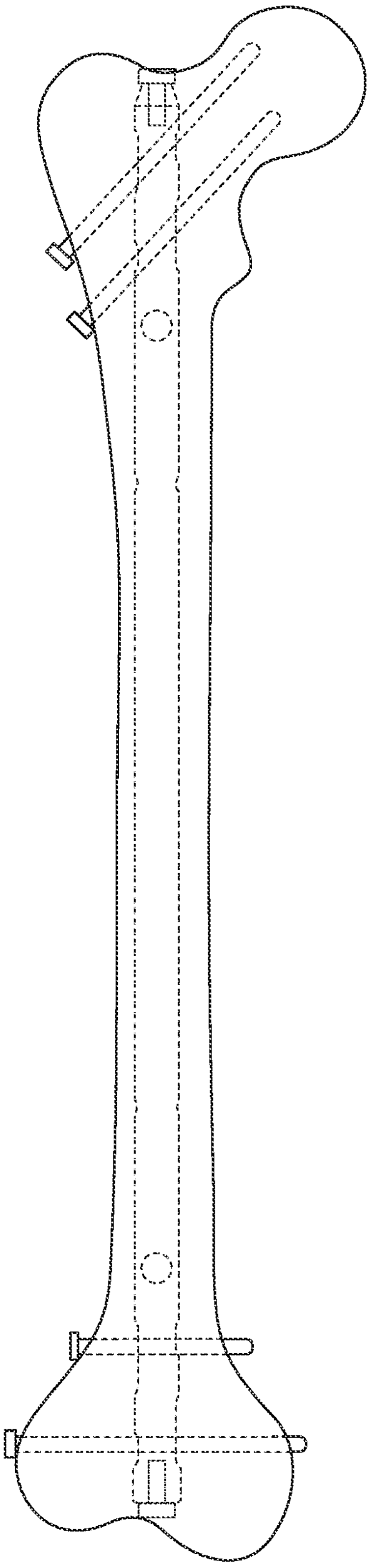

FIG. 6 is a side elevational view of the intramedullary nail illustrating end caps received in both ends of the intramedullary nail positioned in the intramedullary canal of a femur.

Figure 7A:
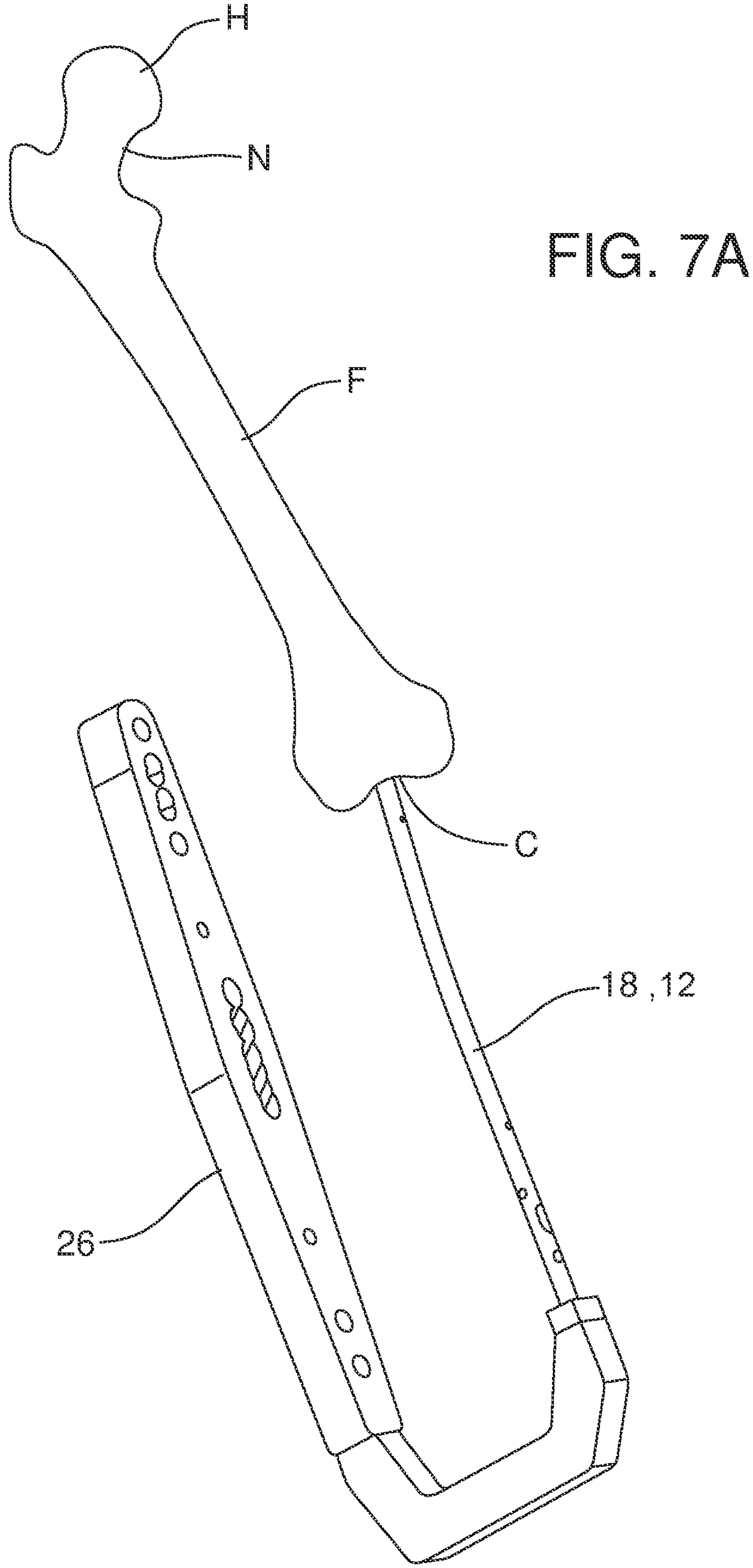
Figure 7B:
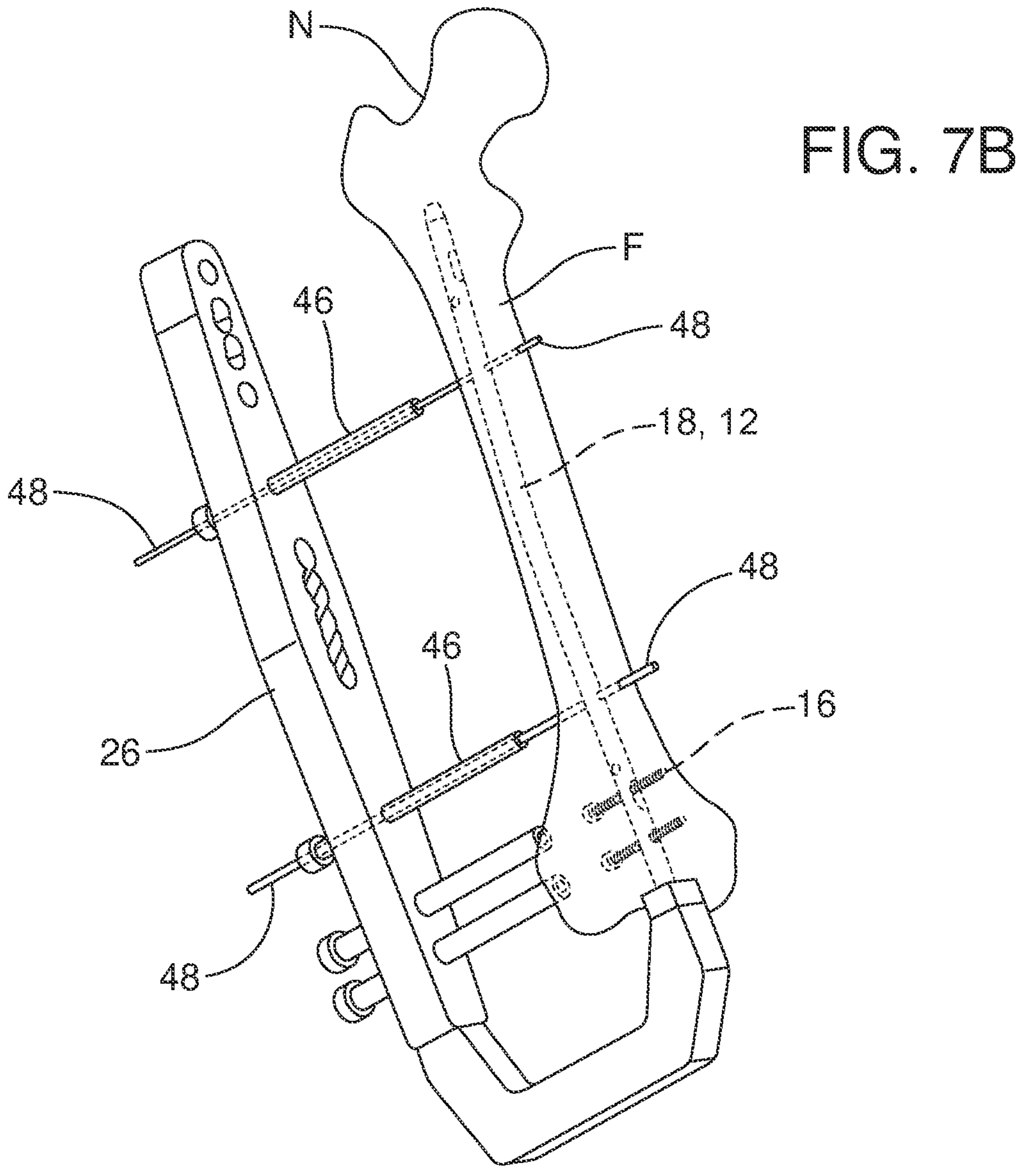
Figure 7C:
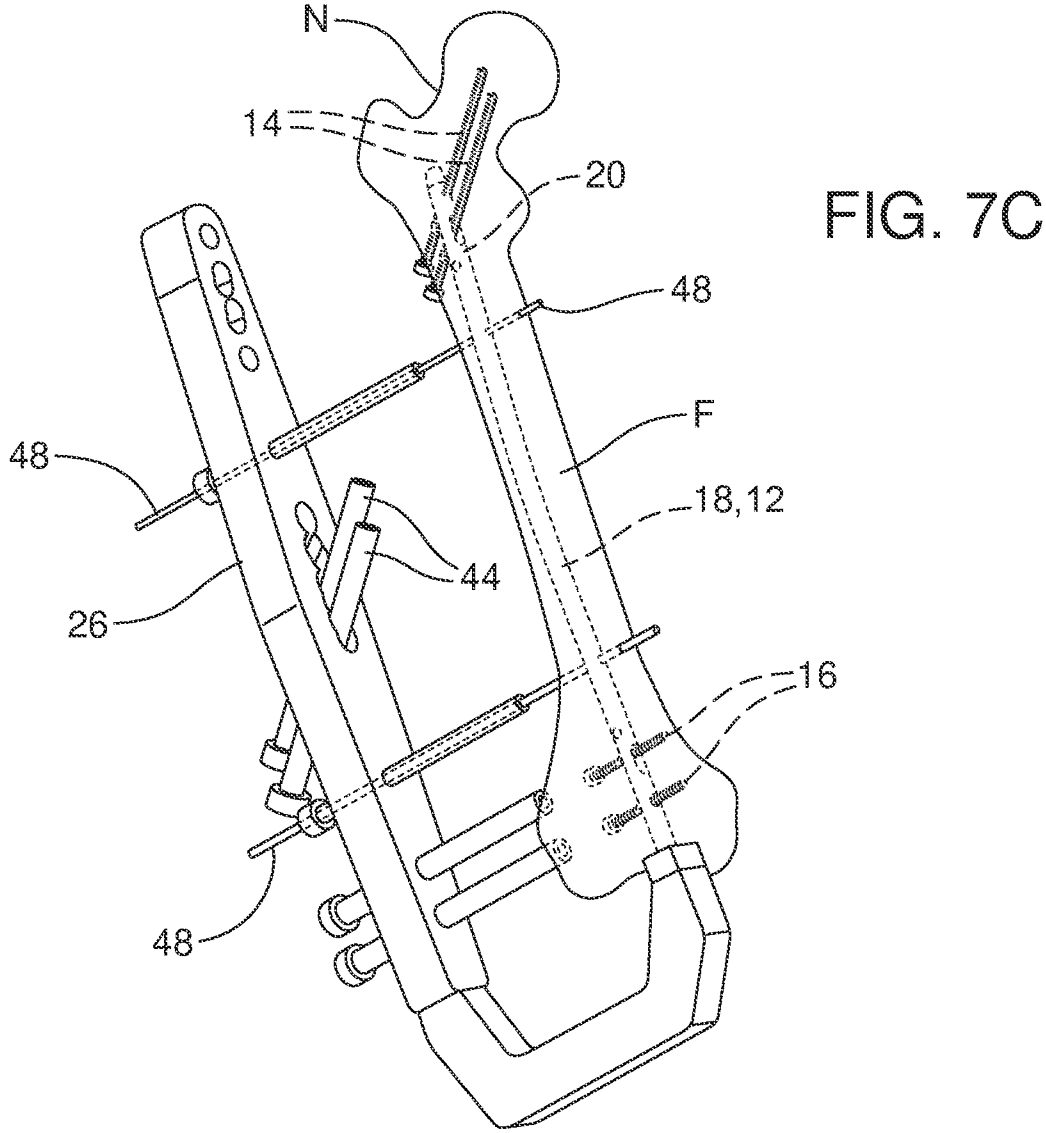

FIGS. 7A-7C illustrate a method of fixing a fractured femur by retrograde insertion of the intramedullary nail into the intramedullary canal, properly aligning an oblique fastener locator in the guide and an oblique fastener receiver in the nail with the native angle of the femoral neck of the fractured femur and engaging at least one fastener at an oblique angle into the neck of the fractured femur.

Figure 8:
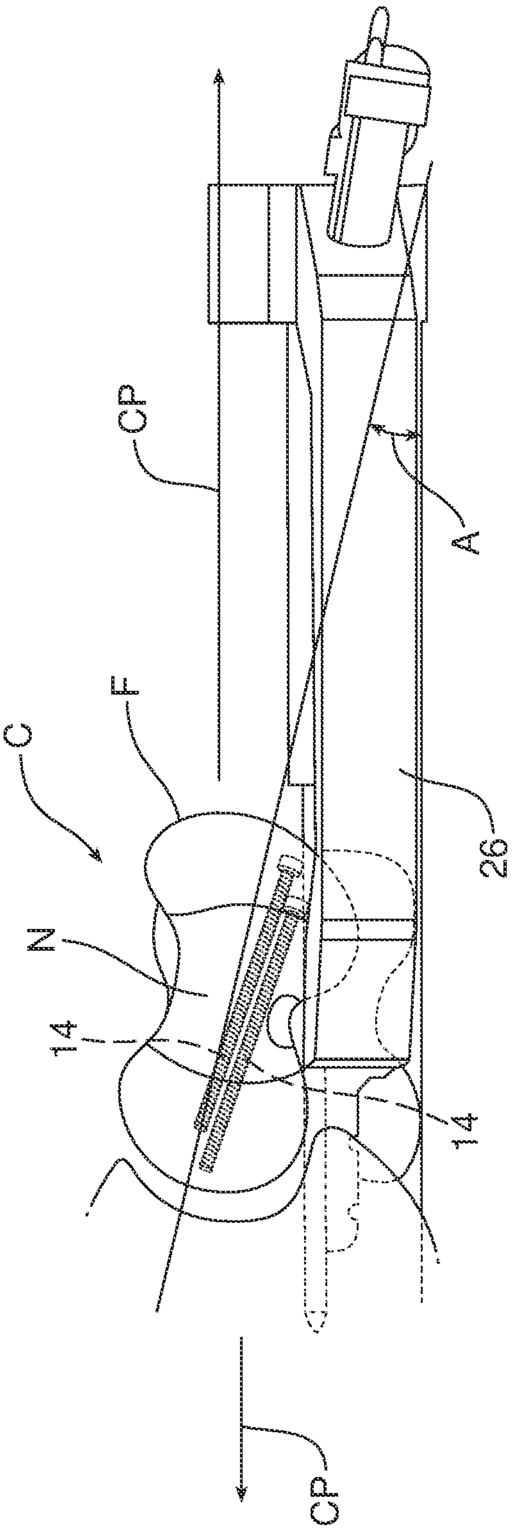

FIG. 8 illustrates the anteversion angle (between the 5 degree and 25 degrees) of the fastener in the femoral neck to match the native angle of the patient's femur.

DETAILED DESCRIPTION

Accordingly, it is to be understood that the embodiments of the femoral intramedullary device 10 and related method of fixing a fractured femur set forth and described herein are merely illustrative and not restrictive. Reference herein to details of the illustrated embodiments is not intended to limit the scope of the claims. As used herein, the term "and/or" includes "and" and all combinations of one or more of the associated listed items. As used herein, the singular forms "a", "an," and "there" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this device and method belong. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the device 10 and method, it will be understood that a number of techniques and steps are disclosed. Each of these had individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of this document and the claims.

Figure 1:
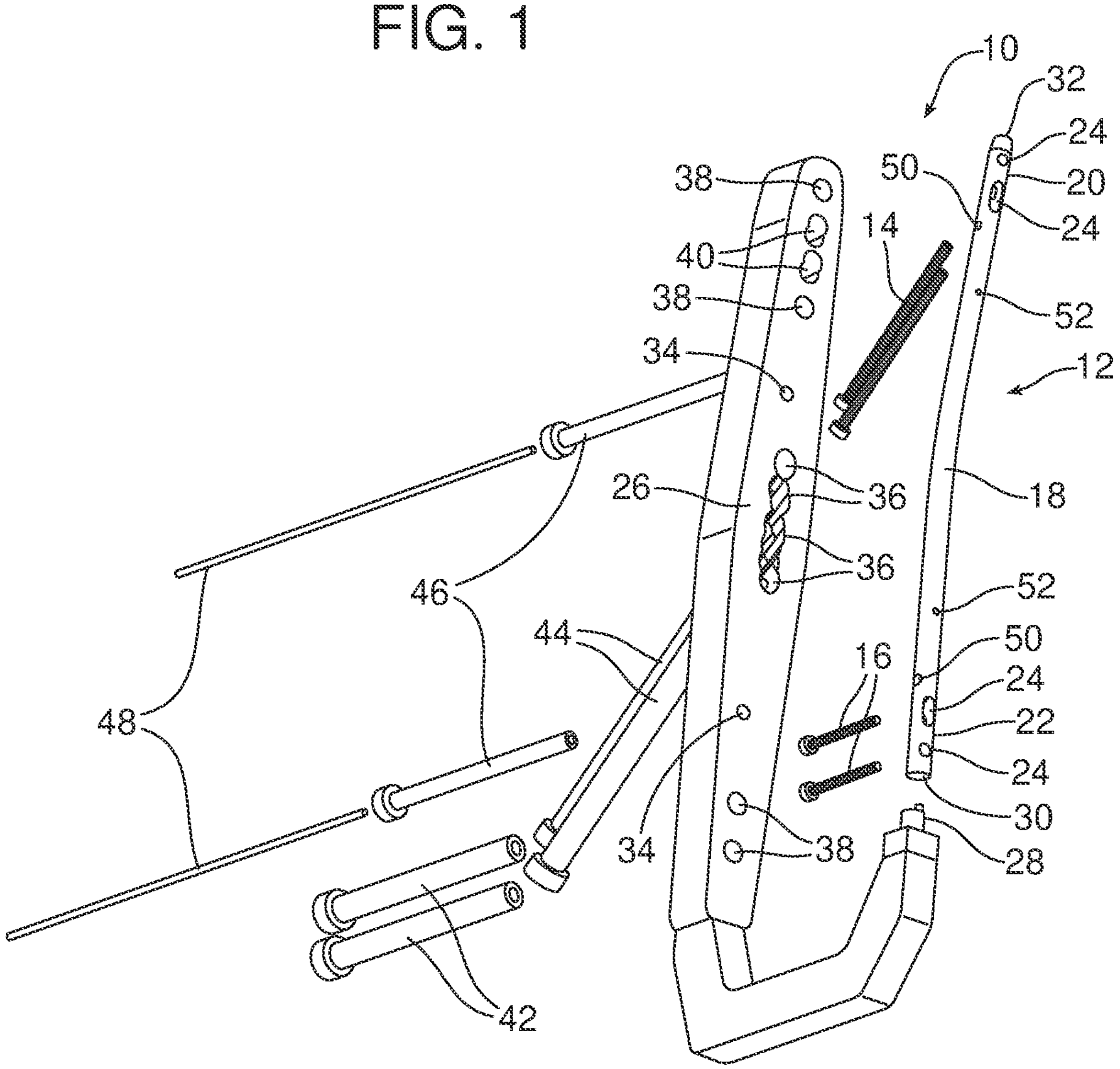
FIG. 1 depicts an exploded longitudinal perspective view of one possible embodiment of the femoral intramedullary device including the guide.

The femoral intramedullary device 10 will now be described by referencing the appended figures representing preferred embodiments. FIG. 1 illustrates the individual components of the device 10. The components are constructed of implantable stainless steel alloys but could also be constructed of implantable grade titanium alloys, as well. Other material having the requisite properties, of strength and inertness may be used. These components consist of the intramedullary nail 12 and the plurality of fasteners 14, 16. As will become apparent from the following description, the intramedullary nail 12 is configured for antegrade or retrograde insertion into a femur. Antegrade insertion is through the hip end of the femur. Retrograde insertion is through the knee end.

The intramedullary nail 12 has an elongated shank or body 18 including a first end 20, a second end 22 and a plurality of oblique fastener receivers 24. At least one oblique fastener receiver 24 is provided at the first end 20 and at least one oblique fastener receiver is provided at the second end 22. In the embodiment illustrated in FIG. 1, two oblique fastener receivers 24 are provided at each end 20, 22.

In FIG. 1, the fasteners 14 are illustrated as oblique interlocking screws and the fasteners 16 are illustrated as transverse interlocking screws. Here it should be appreciated that the fasteners 14, 16 may assume other configurations. Thus, the fasteners 14, 16 may be selected from a group of fasteners useful for the intended purpose(s) of fixing the intramedullary nail 12 in the intramedullary canal of a femur and stabilization of the femoral neck and/or trochanteric regions and/or diaphysis and/or metaphyseal and/or condylar regions of the femur. Such fasteners include, but are not limited to at least one screw, at least one helical blade, at least one bolt, at least one compression screw, at least one wire, at least one pin, at least one bone fixation device and combinations thereof.

The femoral intramedullary device 10 further includes a guide or outrigger 26. In the illustrated embodiment, the guide 26 has a substantially J-shape. The guide 26 includes a lug 28 at a terminal end thereof adapted to engage in a lug receiver 30 in the second end 22 of the elongated body 18 of the intramedullary nail 12. The lug 28 and lug receiver 30 may both be threaded for secure engagement. The first end 20 of the elongated body 18 includes an at least partially tapered tip 32 to aid in inserting the intramedullary nail 12 into the intramedullary canal of a femur. The at least partially tapered tip 32 may take the form of a truncated cone as shown.

As best illustrated in FIG. 1, the guide 26 includes at least one stabilizer pin receiver 34 (two are shown), at least one oblique fastener locator 36 (four are shown) and at least one transverse fastener receiver 38 (four are shown). Two additional oblique fastener locators 40 are also provided near the end of the guide 5 opposite the lug 28.

The femoral intramedullary device 10 may also include one or more transverse guide sleeves 42, one or more oblique guide sleeves 44, and one or more transverse guide sleeves 46 for one or more stabilizer pins 48. As will be described in greater detail below, the stabilizer pins 48 extend through the transverse guide sleeves 46 held in the stabilizer pin receivers 34 and engage in the transverse stabilizer sockets 50 in the intramedullary nail 12.

The guide 26 may be used for placement of the various plurality of fasteners 14, 16 (e.g. screws/blades/pins/wires/drill bits) into the intramedullary nail 12. The guide 26 is constructed from carbon fiber but other material having the requisite properties, of strength, radiolucency, and inertness may be used. The guide sleeves 42, 44, 46 assist with placement of the fasteners 14, 16 and the stabilizer pins 48. The guide 26 may be adapted to have options and/or adjustments to allow a variety of nail lengths, nail insertion methods, and screw/blade/bolt/device placement.

Figure 2A:
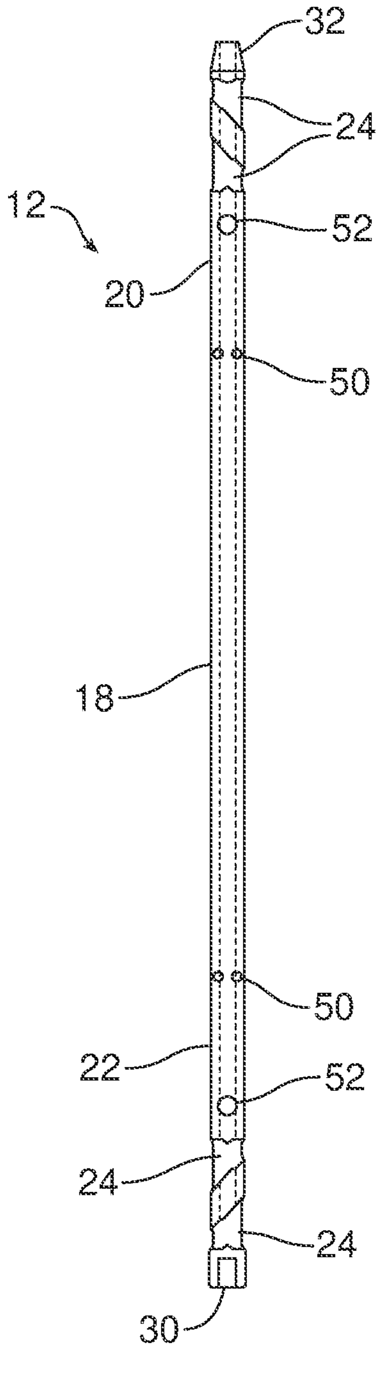
FIG. 2A depicts a direct anterior longitudinal perspective view of the intramedullary nail of the device illustrated in FIG. 1.
Figure 2B:
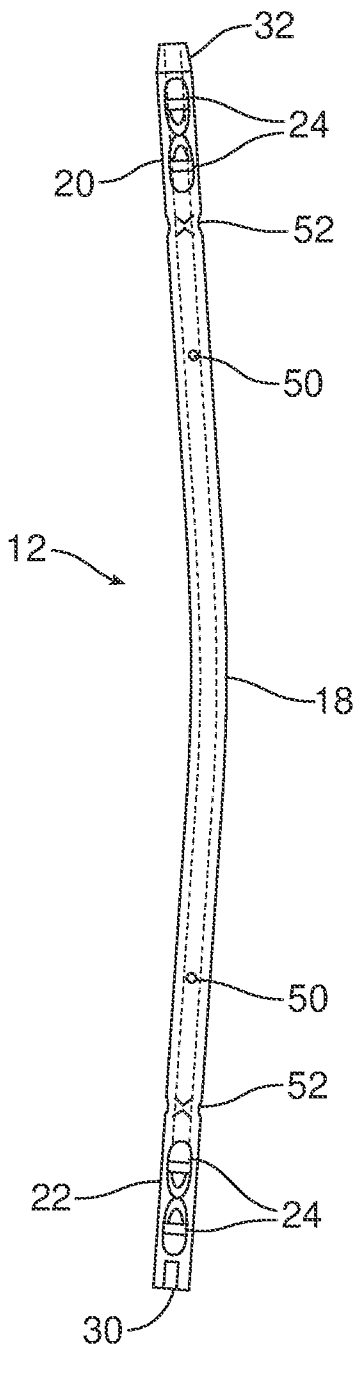
FIG. 2B depicts a direct lateral perspective view of that intramedullary nail illustrated in FIG. 2A.
Figure 2C:
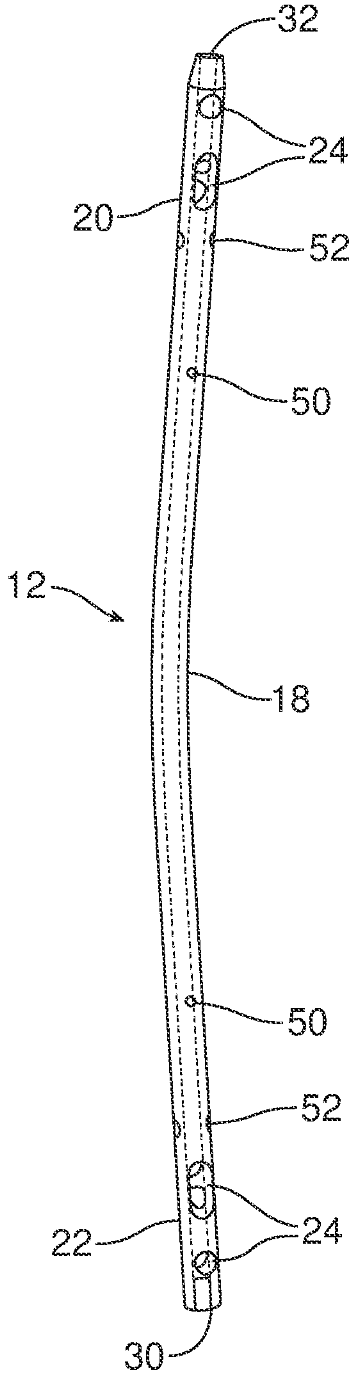
FIG. 2C depicts a lateral, oblique perspective view of the intramedullary nail illustrated in FIGS. 2A and 2B.

The features of the intramedullary nail 12 are best illustrated in FIGS. 2A-2C. The direct anterior view (FIG. 2A) shows the nail 12 as it would appear for retrograde insertion. FIG. 2B depicts a lateral view of the medial side of the nail 12 if inserted in a retrograde fashion in the right femur. If inserted antegrade, FIG. 2B becomes the lateral side of the nail 12 in the right femur. FIG. 2C depicts a lateral view of the lateral side of the nail 12 if inserted in a retrograde fashion in the right femur. If inserted antegrade, FIG. 2C is then a view of the medial side of the nail in the right femur. As illustrated in FIGS. 2A-2C, the elongated body 18 of the intramedullary nail 12 includes two oblique fastener receivers 24 at the first end 20 and two oblique fastener receivers 24 at the second end 22. In addition, one transverse stabilizer socket 50 is provided at each end 20, 22 inboard of the oblique fastener receivers 24. As noted above, the lug receiver 30 at the second end 22 is adapted to connect the intramedullary nail 12 to the guide 26 by means of the lug 28. The tapered tip 32 at the first end 20 may also include a lug receiver if desired.

The oblique fastener receivers 24 allow for the placement of the fasteners 14, 16 in an oblique or transverse fashion. Additional anterior to posterior sockets 52 can be used as additional fixation points in order to help with stabilization of the fracture. More specifically, the sockets 50, 52 allow stabilizer pins 48 to be placed in two different planes (i.e. lateral-to-medial and anterior-to-posterior) that greatly enhances stability. The transverse stabilizer sockets 50 in the body 18 of the nail 12 receive the stabilizer pins 48 and allow for stabilization of the guide 26 with respect to the nail 12 prior to fixation to the femur.

Figure 3:
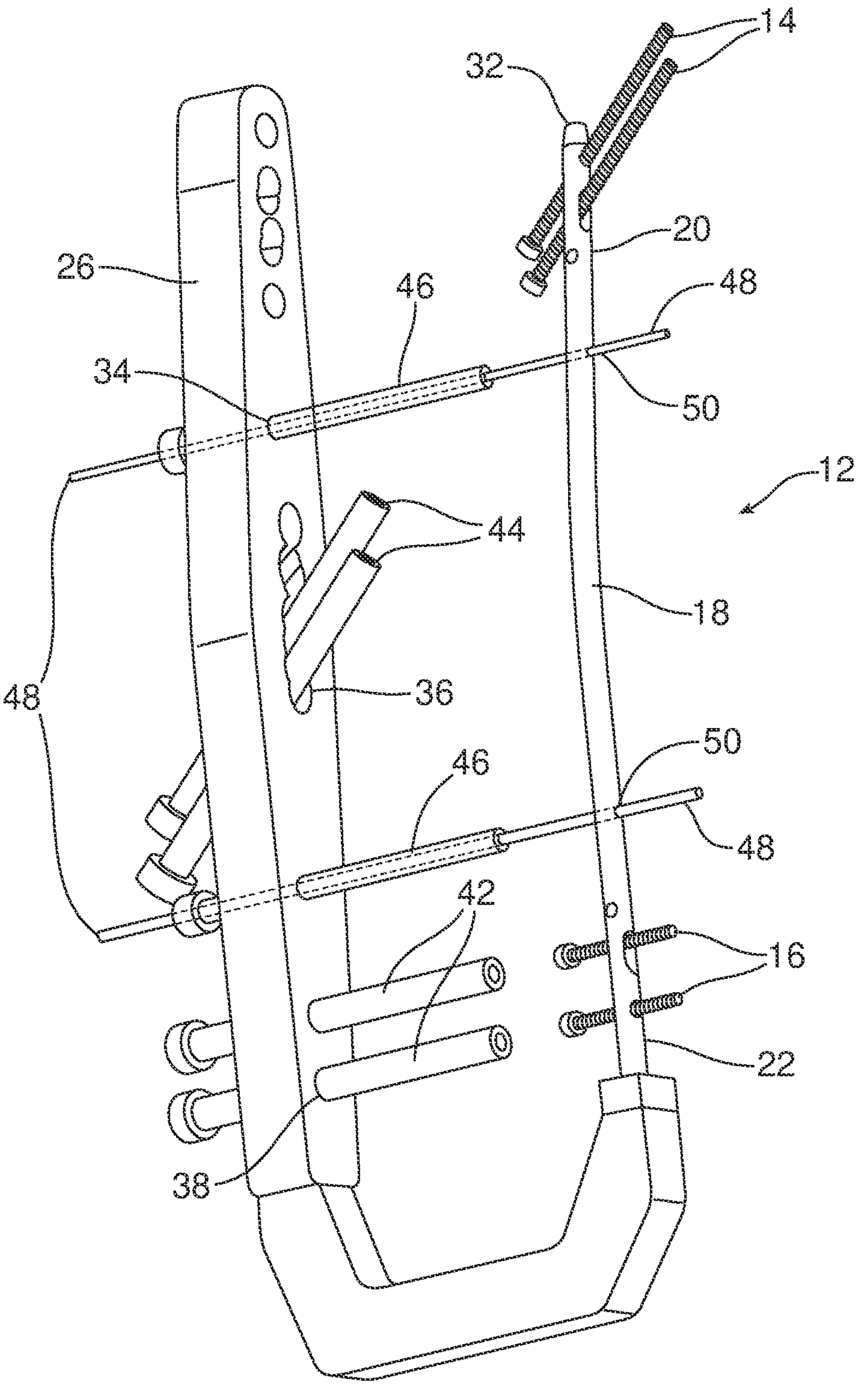
FIG. 3 depicts a longitudinal view of the femoral intramedullary device with attached guide configured for retrograde insertion.

FIG. 3 depicts how the guide 26 may assist with placement of the fasteners 14, 16. After insertion of the nail 12 into a desired position in the intramedullary canal of the femur so as to extend across any fracture line, the attached guide 26 may be stabilized using the stabilizer pins 48. More particularly, the transverse guide sleeves 46 are inserted into the stabilizer pin receivers 34 in the guide 26 so as to extend at least partially between the guide and the nail 12. The stabilizer pin receivers 34, the transverse guide sleeves 46 and the transverse stabilizer sockets 50 are all aligned. The stabilizer pins 48 are then passed through the guide 26, the guide sleeves 46 and then through the cortical bone into the corresponding transverse stabilizer sockets 50 in the nail 12. The use of these additional fixation points is optional with the use of one, two, or all available. To definitively stabilize the nail 12 within the intramedullary canal of the femur, fasteners 14, 16 may then be inserted using oblique and transverse guide sleeves 44, 42 to increase accuracy of placement.

Those guide sleeves 44, 42 are inserted in the respective oblique and transverse fastener locators 36, 38 provided on the guide 26 as illustrated in FIGS. 3 and 5 and extend at least partially between the locators and the oblique fastener receivers 24. The fasteners 14, 16 may be inserted based on location of the fracture(s) and/or patient characteristics and/or desired stabilization of the fracture(s) and/or direction of nail insertion. FIGS. 4A-4C depict various screw configurations but are not intended to describe all possible configurations or limit the scope of this device 10. For example, FIG. 4A depicts nail 12 placement in retrograde fashion with oblique screws 14 at proximal or first end 20 allowing for fixation/stabilization of the femoral neck N, and transverse screws 16 at distal or second end 22.

FIG. 5 depicts how the guide 26 may assist with fastener placement in the antegrade fashion. After insertion of the nail 12 into a desired position the attached guide 26 may be stabilized using stabilizer pins 48 passed through transverse sleeves 46 through the guide 26 and then through cortical bone and through the corresponding sockets 50 in the nail. The use of these additional fixation points is optional with the use of one, two, or all available. To definitively stabilize the nail 12 within the intramedullary canal, fasteners 14, 16 may be inserted using transverse 42 and oblique sleeves 44 to increase accuracy of placement. The fasteners 14, 16 may be inserted based on location of the fracture(s) and/or patient characteristics and/or desired stabilization of the fracture(s) and/or direction of nail insertion.

FIG. 4B depicts the nail 12 inserted in antegrade fashion with oblique screws 14 at the proximal or first end 20 allowing for fixation/stabilization of the femoral neck N, and transverse screws 16 at the distal or second end 22. FIG. 4C depicts the nail 12 placed in antegrade fashion with one oblique screw 14 placed at the proximal or first end 20 with additional screw 58 placement in anterior to posterior fashion with transverse screws 16 to stabilize the distal or second end 22. Other combinations or configurations of fasteners 14, 16, 58 may be used depending upon the needs of any particular application.

The femoral intramedullary device 10 described above and illustrated in the drawing figures is useful in a new and improved method of fixing a fractured femur F. That method includes the step of mounting the intramedullary nail 12 onto the guide 26 by engaging the lug 28 on the guide in the lug receiver 30 in the second end 22 of the nail. The method also includes the step of orienting the intramedullary nail 12, that is configured for either antegrade or retrograde insertion, for insertion into the intramedullary canal of the femur. This is followed by inserting the intramedullary nail into the intramedullary canal so as to extend across the fracture line of the femur. This insertion may be in an antegrade direction or a retrograde direction depending upon the application.

FIG. 6 illustrates end caps 60 that may be attached by threaded connection into the ends of the intramedullary nail 12 to prevent ingrowth of tissue. As illustrated, the end caps 60 may also engage the endmost fasteners 14, 16 to help lock those fasteners in position. The end caps 60 also facilitate the extraction of the intramedullary nail 12 from the intramedullary canal of a femur should extraction ever be desired.

The method also includes the step of engaging at least one fastener 14 in an oblique fastener receiver 24 (a) in a first end 20 of the nail to stabilize a neck N of the femur F when the nail is retrograde inserted into the femur (see FIGS. 3 and 4A) or (b) in a second end 22 of the nail to stabilize a neck N of the femur F when the nail is antegrade inserted into the femur (see FIGS. 4B and 5).

The method may also include the step of inserting a stabilizer pin 48 into a stabilizer pin receiver 34 in the guide 26 and a transverse stabilizer socket 50 of the nail 12 in order to (a) stabilize the nail in the intramedullary canal of the femur F and to (b) properly align an oblique fastener locator 36 in the guide with an oblique fastener receiver 24 in the first end 20 when the nail is retrograde inserted into the femur and in the second end 22 when the nail is antegrade inserted into the femur.

Toward this end, the method may include the step of positioning a transverse guide sleeve 46 in the stabilizer pin receiver 34 in the guide 26 so as to at least partially extend between the stabilizer pin receiver in the guide and the transverse stabilizer socket 50 in the nail. The stabilizer pin 48 is then pushed through the transverse guide sleeve 46 into and through the transverse stabilizer socket 50.

The method may also include the step of positioning an oblique guide sleeve 44 into the oblique fastener locator 36 of the guide 26 so as to extend at least partially between the oblique fastener locator and the oblique fastener receiver 24 in the nail. The oblique fastener 14 is inserted using the sleeve 44 so that the fastener engages in the oblique fastener receiver 24 (a) in the first end 20 of the nail 12 to stabilize the neck N of the femur F when the nail is retrograde inserted into the femur or (b) in the second end 22 of the nail to stabilize the neck of the femur when the nail is antegrade inserted into the femur. As a result, the method also includes the step of extending at least one fastener 14 into the neck N of the femur F to thereby stabilize that neck.

A transverse guide sleeve 42 may be used in a similar manner in order to place a transverse fastener 16.

Reference is now made to FIGS. 7A-7C, which illustrate a new and improved method for fixing the femoral neck N of a fractured femur F. As best illustrated in FIG. 7A, that method includes mounting the intramedullary nail 18 onto a guide 26 by engaging a lug 28 on the guide with a lug receiver 30 at the second end 22 of the intramedullary nail prior to the orienting of the intramedullary nail 12 as previously described and shown in FIG. 1. The lug 28 is adapted to ensure that the oblique fastener locators 36 in the guide 26 align with the oblique fastener receiver 24 in the intramedullary nail 12.

This is followed by orienting the intramedullary nail 12 for retrograde insertion into an intramedullary canal of the fractured femur F. Toward this end, the method includes using a center of a intercondylar notch N in a coronal plane CP of the fractured femur as a starting point (see also FIG. 8) and inserting a first end 20 of the intramedullary nail 12 into the intramedullary canal so as to extend across a fracture line of the fractured femur F. See also FIG. 7B.

As shown in FIG. 7B, the method includes inserting a stabilizer pin 48 (two shown in FIG. 7B) into a stabilizer pin receiver 34 in the guide 26 and a transverse stabilizer socket 52 of the intramedullary nail 12 to stabilize the intramedullary nail in the intramedullary canal of the fractured femur F and to properly align an oblique fastener locator 36 in the guide with an oblique fastener receiver 24 in the first end 20 of the intramedullary nail. Toward this end, the method includes positioning a transverse guide sleeve 46 between the stabilizer pin receiver 34 in the guide 26 and the transverse stabilizer socket 52 in the intramedullary nail 12 prior to inserting the stabilizer pin 48.

As shown in FIG. 7C, the method also includes positioning an oblique guide sleeve 44 between the oblique fastener locator 36 in the guide 26 and the oblique fastener receiver 24 in the intramedullary nail 12. This is followed by engaging at least one fastener 14 (two are shown in the drawing Figure) in the oblique fastener receivers 24 in the first end 20 of the intramedullary nail 12 to stabilize the neck N of the fractured femur F.

Reference is now made to FIG. 8 which clearly shows how the fasteners 14 received in the femoral neck N extend at an anteversion angle A to match or substantially match the native angle of the femoral neck N. That anteversion angle A may be between about 5 degrees and about 25 degrees. More typically, that anteversion angle A is between about 10 degrees and about 20 degrees. In many embodiments, that anteversion angle A is about 15 degrees. As should be appreciated the oblique fastener locator(s) 36 in the guide 26, the oblique fastener receiver(s) 24 in the intramedullary nail 12 and the fastener(s) 14 ultimately engaged in the femoral neck N are all aligned at the anteversion angle A that substantially matches the native angle of the femoral neck N and falls on a line forming an acute included anteversion angle A of between about 5 degrees and about 25 degrees with the coronal plane CP of the fractured femur F.

Although the femoral intramedullary device 10 and related method have been illustrated and described herein with reference to preferred embodiments and specific examples thereof, it will be readily apparent to those of ordinary skill in the art that other embodiments and examples may perform similar functions and/or achieve like results. All such equivalent embodiment and examples are within the spirit and score of the present invention, are contemplated thereby, and are intended to be covered by the following claims.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:

1. A method of fixing a fractured femur, comprising:

mounting an intramedullary nail onto a guide by engaging a lug on the guide with a lug receiver at a second end of the intramedullary nail:

orienting the mounted intramedullary nail for retrograde insertion into an intramedullary canal of the fractured femur;

using a center of a intercondylar notch in a coronal plane of the fractured femur as a starting point and inserting a first end of the intramedullary nail into the intramedullary canal so as to extend across a fracture line of the fractured femur;

positioning a transverse guide sleeve between a stabilizer pin receiver in the guide and a transverse stabilizer socket in the intramedullary nail;

inserting a stabilizer pin into the stabilizer pin receiver in the guide, the transverse guide sleeve, and the transverse stabilizer socket of the intramedullary nail to stabilize the intramedullary nail in the intramedullary canal of the fractured femur and to properly align an oblique fastener locator in the guide with an oblique fastener receiver in the first end of the intramedullary nail; and engaging at least one fastener at an oblique angle into a neck of the fractured femur.

2. The method of claim 1, including positioning an oblique guide sleeve between the oblique fastener locator in the guide and the oblique fastener receiver in the intramedullary nail before engaging the at least one fastener in the oblique fastener receiver in the first end of the intramedullary nail to stabilize the neck of the fractured femur.

3. The method of claim 2, including extending the at least one fastener into the neck of the fractured femur to thereby stabilize the neck.

4. A femoral intramedullary system, comprising:

an intramedullary nail having a first end configured for retrograde insertion into a fractured femur, the intramedullary nail having an elongated body including at least one oblique fastener receiver at the first end, wherein that at least one fastener receiver is adapted to match a native angle of a femoral neck of the fractured femur when the fractured femur has been realigned for setting; and at least one fastener received in the at least one oblique fastener receiver and the femoral neck of the fractured femur to stabilize a neck of the femur;

wherein the femoral intramedullary system further includes (a) a guide adapted for placement of the at least one fastener with respect to the intramedullary nail (b) at least one stabilizer pin receiver in the guide aligned with at least one transverse stabilizer socket in the elongated body, (c) a transverse guide sleeve extending at least partially between the at least one stabilizer pin receiver in the guide and the at least one transverse stabilizer socket in the intramedullary nail, and (d) at least one stabilizer pin received in the at least one stabilizer pin receiver, the transverse guide sleeve, and the at least one transverse stabilizer socket whereby the intramedullary nail is stabilized in an intramedullary canal of the femur and the at least one oblique fastener locator is properly aligned with the at least one oblique fastener receiver.

5. The femoral intramedullary system of claim 4, wherein the guide is a J-shaped outrigger including a lug at a terminal end thereof adapted to engage in a lug receiver in a second end of the intramedullary nail.

6. The femoral intramedullary system of claim 5, further including an oblique guide sleeve extending at least partially between the at least one oblique fastener locator in the guide and the at least one oblique fastener receiver in the intramedullary nail.

7. The femoral intramedullary system of claim 4, wherein the oblique fastener locator and the oblique fastener receiver are aligned to match a native angle of a femoral neck of the fractured femur at an anteversion angle of between 5 degrees and 25 degrees.

8. The femoral intramedullary system of claim 4, wherein the oblique fastener locator and the oblique fastener receiver are aligned to match a native angle of a femoral neck of the fractured femur at an anteversion angle of between 10 degrees and 20 degrees.

9. The femoral intramedullary system of claim 4, wherein the oblique fastener locator and the oblique fastener receiver are aligned to match a native angle of a femoral neck of the fractured femur at an anteversion angle of 15 degrees.

10. The femoral intramedullary system of claim 4, wherein the oblique fastener receiver is adapted to extend on a line forming an acute included angle of between 5 degrees and 25 degrees with a coronal plane the fractured femur.

* * * * *